United States Patent
Bell et al.

(10) Patent No.: US 9,456,599 B2
(45) Date of Patent: Oct. 4, 2016

(54) ADJUVANTS

(71) Applicant: SYNGENTA LIMITED, Guildford Surrey (GB)

(72) Inventors: Gordon Alastair Bell, Bracknell Berkshire (GB); Julia Lynne Ramsay, Bracknell Berkshire (GB); Nicholas Igor Nouvel, Bracknell Berkshire (GB)

(73) Assignee: Syngenta Limited, Guildford Surrey (GB)

( * ) Notice: Subject to any disclaimer, the term of this patent is extended or adjusted under 35 U.S.C. 154(b) by 0 days.

(21) Appl. No.: 14/431,531

(22) PCT Filed: Oct. 10, 2013

(86) PCT No.: PCT/EP2013/071218
§ 371 (c)(1),
(2) Date: Mar. 26, 2015

(87) PCT Pub. No.: WO2014/057064
PCT Pub. Date: Apr. 17, 2014

(65) Prior Publication Data
US 2015/0250163 A1    Sep. 10, 2015

(30) Foreign Application Priority Data
Oct. 12, 2012 (GB) .................................. 1218407.3

(51) Int. Cl.

| | |
|---|---|
| *A01N 25/00* | (2006.01) |
| *A01N 25/30* | (2006.01) |
| *C07C 69/96* | (2006.01) |
| *A01N 41/06* | (2006.01) |
| *A01N 41/10* | (2006.01) |
| *A01N 43/653* | (2006.01) |
| *A01N 43/90* | (2006.01) |
| *A01N 45/02* | (2006.01) |
| *A01N 47/36* | (2006.01) |

(52) U.S. Cl.
CPC .............. *A01N 25/00* (2013.01); *A01N 25/30* (2013.01); *A01N 41/06* (2013.01); *A01N 41/10* (2013.01); *A01N 43/653* (2013.01); *A01N 43/90* (2013.01); *A01N 45/02* (2013.01); *A01N 47/36* (2013.01); *C07C 69/96* (2013.01)

(58) Field of Classification Search
None
See application file for complete search history.

(56) References Cited

U.S. PATENT DOCUMENTS

| | | | |
|---|---|---|---|
| 6,800,247 B1 * | 10/2004 | Suh ..................... | A01N 43/08 |
| | | | 422/28 |
| 2005/0026780 A1 * | 2/2005 | Parrish ................. | A01N 25/10 |
| | | | 504/119 |
| 2008/0305952 A1 * | 12/2008 | Arnevik ................ | A01N 25/00 |
| | | | 504/127 |
| 2011/0105373 A1 | 5/2011 | Tsubouchi et al. | |
| 2012/0053221 A1 | 3/2012 | Ishaque et al. | |
| 2012/0054920 A1 | 3/2012 | Tuerk et al. | |

FOREIGN PATENT DOCUMENTS

| | | |
|---|---|---|
| EP | 2409568 A1 | 1/2012 |
| JP | 2000319111 | * 11/2000 |
| WO | 9929170 A1 | 6/1999 |
| WO | 0217722 A2 | 3/2002 |
| WO | 2012146889 A1 | 11/2012 |

OTHER PUBLICATIONS

Cross et al., Field Tests of Uniforms Impregnated with Mite Toxicants: I, Protection Studies, Journal of Economic Entomology, vol. 41, No. 6, Dec. 1948, pp. 936-940.*
Cross et al., Use of Powders on Clothing for Protection Against Chiggers, Journal of Economic Entomology, vol. 41, No. 5, Oct. 1948, pp. 731-734.*
International Search Report, Mail Date Sep. 11, 2014, for international application No. PCT/EP2013/071218.

* cited by examiner

*Primary Examiner* — Jennifer Berrios
(74) *Attorney, Agent, or Firm* — James Cueva

(57) ABSTRACT

This invention relates to a composition comprising an agrochemical and a compound of formula (I) wherein each A is independently selected from $C_{1-10}$ alkanediyl; n is an integer selected from 0 to 45 inclusive; and m is an integer selected from 1, 2, 3 and 4; R is a branched or linear $C_1$-$C_{24}$ hydrocarbon either fully saturated or comprising up to three double bonds or is phenyl or is benzyl or is a $C_3$-$C_8$ fully saturated cyclic group; and R is substituted 1, 2, 3 or 4 times as defined by the value of m; and when m is 1 and n is not zero, R may also be hydrogen; and Q is a branched or linear $C_1$-$C_{24}$ hydrocarbon either fully saturated or comprising up to three double bonds or is phenyl or is benzyl or is a $C_3$-$C_8$ fully saturated cyclic group; provided that when m is 1 and n is zero, Q and R are not both selected from a branched or linear $C_1$-$C_{24}$ hydrocarbon either fully saturated or comprising up to three double bonds to methods of making and using the compositions; and to the use of the compounds as adjuvants for agrochemical use. In particular the present invention relates to compositions selected from an emulsion concentrate (EC), an emulsion in water (EW), a suspension of particles in water (SC), a soluble liquid (SL), a microcapsule formulation (CS), a suspension of particles with an emulsion (SE), a dispersion concentrate (DC), an oil suspension (OD), a water dispersible granule (WG), a soluble granule (SG) and a wettable powder (WP).

$$\left[ Q\diagup\mathrm{O}\diagdown\underset{\mathrm{O}}{\overset{}{\mathrm{C}}}\diagdown\mathrm{O}\!-\!\!\left(\mathrm{AO}\right)_{\!n}\!\!-\!\!\mathrm{R}\right]_{m} \quad (I)$$

10 Claims, No Drawings

ADJUVANTS

RELATED APPLICATION INFORMATION

This application is a 371 of International Application No. PCT/EP2013/071218, filed 10 Oct. 2013, which claims priority to GB Patent Application 1218407.3, filed 12 Oct. 2012, the contents of which are incorporated herein by reference herein.

This invention relates to novel carbonate compounds; to compositions comprising the novel compounds; to methods of making and using the compositions; and to the use of the novel compounds as adjuvants, particularly for agrochemical use. In particular the present invention relates to compositions selected from an emulsion concentrate (EC), an emulsion in water (EW), a suspension of particles in water (SC), a soluble liquid (SL), a microcapsule formulation (CS), a suspension of particles with an emulsion (SE), a dispersion concentrate (DC), a suspension of particles in oil (OD), a water dispersible granule (WG), a soluble granule (SG) and a wettable powder (WP).

The efficacy of a biologically active ingredient (AI), for example an agrochemical, in a composition can often be improved by the addition of further ingredients. The observed efficacy of the combination of ingredients can sometimes be significantly higher than that which would be expected from the individual ingredients used (synergism). An adjuvant is a substance which can increase the biological activity of an AI but is itself not significantly biologically active. The adjuvant is often a surfactant, and may be included in a formulation or added separately, (often referred to as being built into formulations or as tank mix additives).

In addition to the effect on biological activity, the physical properties of an adjuvant are of key importance and must be selected with a view to compatibility with the formulation concerned. For instance, it is generally simpler to incorporate a solid adjuvant into a solid formulation such as a water-soluble or water-dispersible granule. In general adjuvants rely on surfactant properties for biological activity enhancement and one typical class of adjuvants involves an alkyl or aryl group to provide a lipophilic moiety and a (poly)ethoxy chain to provide a hydrophilic moiety. Much has been published on the selection of adjuvants for various purposes, such as Hess, F. D. and Foy, C. L., Weed technology 2000, 14, 807-813.

The present invention is based on the discovery that certain carbonate compounds are surprisingly effective adjuvants, significantly enhancing the biological activity of active ingredients.

The present invention provides novel carbonate compounds of formula (I)

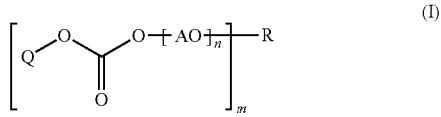

wherein
each A is independently selected from $C_{1-10}$ alkanediyl; n is an integer selected from 0 to 45 inclusive; and m is an integer selected from 1, 2, 3 and 4; R is a branched or linear $C_1$-$C_{24}$ hydrocarbon either fully saturated or comprising up to three double bonds or is phenyl or is benzyl or is a $C_3$-$C_8$ fully saturated cyclic group; and R is substituted 1, 2, 3 or 4 times as defined by the value of m; and when m is 1 and n is not zero, R may also be hydrogen; and Q is a branched or linear $C_1$-$C_{24}$ hydrocarbon either fully saturated or comprising up to three double bonds or is phenyl or is benzyl or is a $C_3$-$C_8$ fully saturated cyclic group; provided that when m is 1 and n is zero, Q and R are not both selected from a branched or linear $C_1$-$C_{24}$ hydrocarbon either fully saturated or comprising up to three double bonds. Alternatively, when n is zero, Q and R are not the same.

Other than the substituents defined above, R is not further substituted. Similarly, Q carries no further substituents.

In a second aspect the present invention provides a composition comprising a biologically active ingredient (preferably an agrochemical) and a compound of formula (I).

In a third aspect the present invention provides the use of a compound of formula (I) as described herein as an adjuvant for a biologically active ingredient (preferably an agrochemical)

In a further aspect the invention provides the use of an agrochemical composition as described herein to control pests.

In a still further aspect there is provided a method of controlling a pest, comprising applying a composition of the invention to said pest or to the locus of said pest.

In a yet further aspect there is provided a method of making an agrochemical composition as described herein, comprising combining a biologically active ingredient and compound of formula (I).

Q and R may each, independently, be a $C_1$-$C_{24}$ hydrocarbon which may be an alkyl group, an alkenyl group, an alkyldienyl group or an alkyltrienyl group.

Alkyl groups and moieties are straight or branched chains, and unless explicitly stated to the contrary, are unsubstituted. Examples of suitable alkyl groups for use in the invention are methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups.

Alkenyl groups and moieties are straight or branched chains having a single carbon-carbon double bond, and unless explicitly stated to the contrary, are unsubstituted. Examples of suitable alkenyl groups for use in the invention are but-1-enyl, pent-1-enyl, hex-1-enyl, hept-1-enyl, hept-2-enyl, hept-3-enyl, oct-1-enyl, non-1-enyl, dec-1-enyl, undec-1-enyl, and groups derived from monoenoic fatty acids including cis-4-decenyl, cis-9-decenyl, cis-4-dodecenyl, cis-9-tetradecenyl, cis-5-tetradecenyl, cis-4-tetradecenyl, cis-9-hexadecenyl, cis-6-hexadecenyl, cis-6-octadecenyl, cis-9-octadecenyl, trans-9-octadecenyl, cis-11-octadecenyl, cis-9-eicosenyl, cis-11-eicosenyl, cis-11-docosenyl, cis-13-docosenyl and cis-15-tetracosenyl.

Alkyldienyl groups and moieties are straight or branched chains having two carbon-carbon double bonds, and unless explicitly stated to the contrary, are unsubstituted. Examples of suitable alkyldienyl groups for use in the invention are hept-1,3-dienyl, linoleyl, and linoelaidyl.

Alkyltrienyl groups and moieties are straight or branched chains having three carbon-carbon double bonds, and unless explicitly stated to the contrary, are unsubstituted. Examples of suitable alkyldienyl groups for use in the invention are hex-1,3,5-trienyl, hepta-1,3,5-trienyl and linolenyl.

The term alkanediyl defines bivalent straight or branch chained hydrocarbon radicals, such as methylene, 1,2-ethanediyl, 1,1-ethanediyl, 1,3-propanediyl, 1,1-propanediyl, 1,2-propanediyl, 1,4-butanediyl and 1,5-pentanediyl.

In particularly preferred embodiments of the invention, the preferred values for m, and n as well as the preferred groups for R, in any combination thereof (unless specifically stated otherwise) are as set out below.

Suitably R is a branched or linear $C_1$-$C_{24}$ hydrocarbon either fully saturated or comprising up to three double bonds or is a $C_3$-$C_8$ fully saturated cyclic group; and R is substituted 1, 2, 3 or 4 times as defined by the value of m. More suitably, R is a branched or linear $C_8$-$C_{20}$ hydrocarbon either fully saturated or comprising up to three double bonds; even more suitably it is a branched or linear $C_{16}$-$C_{20}$ hydrocarbon either fully saturated or comprising up to three double bonds.

In one preferred embodiment, R is oleyl.

Suitably Q is a branched or linear $C_1$-$C_{24}$ hydrocarbon either fully saturated or comprising up to three double bonds or is phenyl or is benzyl. Preferably Q is phenyl, benzyl or 2-ethylhexyl; more preferably Q is phenyl or is benzyl.

Preferably m is 1, 2 or 3; more preferably m is 1 or 2; most preferably m is 1.

Suitably each A is independently a $C_2$-$C_4$ alkanediyl group. Preferably each A is independently a $C_1$-$C_4$ alkanediyl group, more preferably each A is independently ethanediyl, propanediyl or butanediyl, more preferably still each A is independently 1,2-ethanediyl, 1,2-propanediyl, 1,2-butanediyl or 1,4-butanediyl; 1,2-ethanediyl is most preferred.

Suitably n is an integer selected from 0 to 30 inclusive. Preferably n is an integer selected from 0 to 20 inclusive; more preferably from 0 to 10 inclusive; even more preferably from 2 to 10 inclusive.

Where m is 2, 3 or 4, each group

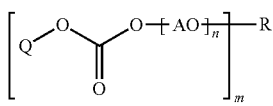

may be the same or different (i.e. each Q, A and n is independently selected); suitably, each group is the same. Furthermore, each group is independently attached to any carbon atom in R; in certain embodiments, each group is attached to a different carbon atom in R.

In further embodiments, when m is 2, 3 or 4, R is $C_3$-$C_{18}$ alkyl, more preferably, $C_3$-$C_{17}$ alkyl, more preferably $C_3$-$C_8$ alkyl, $C_{12}$-$C_{15}$ alkyl, $C_{16}$ alkyl, or $C_{17}$ alkyl. In certain embodiments wherein m is 2, R is a $C_8$ branched chain alkyl group. In certain embodiments wherein m is 3, R is trivalent $C_3$-$C_8$ alkyl, such as a glycerol derivative (i.e. —$CH_2$(CH—)$CH_2$—). In other embodiments wherein m is 4, R is tetravalent $C_3$-$C_8$ alkyl, such as a pentaerythritol derivative (i.e. C($CH_2$—)$_4$).

In one embodiment, there is provided an agrochemical composition comprising (i) an active ingredient, (ii) a surfactant, and (iii) a carbonate of formula (I).

An additional advantage of functionalising alkane/alkene ethoxylate molecules with a carbonate end group, such as benzyl or phenyl carbonate, is the lowering of the melting point. For example PEG-2 oleyl ether, which is a product commercialised by Croda under the trade name BRIJ™ O2-LQ-(MV) is a paste or waxy solid at room temperature but once functionalised with either a benzyl carbonate (B92-B-carbonate) or a phenyl carbonate (B92-P-carbonate), it becomes a liquid at room temperature. Moreover, the phenyl carbonate functionalisation provides a greater depression of the melting point than benzyl carbonate. This is illustrated by the fact that PEG-10 oleyl ether, which is a product commercialised by Croda under the trade name BRIJ™ O10-SS-(RB) is a paste or waxy solid at room temperature and only becomes a liquid at room temperature when functionalised with a phenyl carbonate moiety (B92-P-carbonate). The benzyl carbonate functionalisation does not sufficiently depress the melting point to affect the physical form of the starting material.

Being liquid confers certain advantages on the adjuvants of the present invention; for example, they are easier to handle and to weigh out, particularly on a large scale.

The carbonates of formula (I) as defined above could find applications as easy to handle adjuvants, with improved build-in properties, for agrochemical, cosmetic or pharmaceutical formulations.

Compounds of formula (I) may be prepared according to reaction scheme 1.

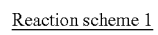

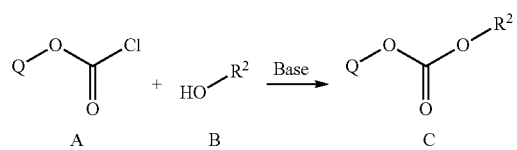

In an appropriate solvent system, a chloroformate (A) is added to an alcohol of formula (B) in the presence of a base to form a carbonate compound (C), which corresponds to a compound of formula (I) where $R^2$ is the group -[AO]$_n$—R; wherein Q, A, n and R are as defined hereinbefore.

Alcohols of formula (B) and chloroformates of formula (A) are readily available or may be synthesised using standard methodology well known in the art.

The present invention is based on the unexpected finding that compounds of formula (I) are particularly good adjuvants for biologically active ingredients, such as agrochemicals, pharmaceuticals and cosmetics and they may be especially effective in agrochemical formulations. Accordingly, in one aspect, the invention provides the use of a carbonate of formula (I) as described herein as a synergist in an agrochemical composition.

Accordingly, such adjuvants may be combined with an active ingredient, which is suitably an agrochemical, in order to form a composition, suitably an agrochemical composition. The present invention extends to a method of making such a composition, wherein said method comprises combining a compound of formula (I) with a biologically active ingredient, and optionally a surfactant. The noun "agrochemical" and term "agrochemically active ingredient" are used herein interchangeably, and they include herbicides, insecticides, nematicides, molluscicides, fungicides, plant growth regulators and safeners; preferably herbicides, insecticides and fungicides.

Suitable herbicides include pinoxaden, bicyclopyrone, mesotrione, fomesafen, tralkoxydim, napropamide, amitraz, propanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyclodim, sethoxydim, tepraloxydim, pendimethalin, dinoterb, bifenox, oxyfluorfen, acifluorfen, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron and metoxuron.

Suitable fungicides include isopyrazam, mandipropamid, azoxystrobin, trifloxystrobin, kresoxim methyl, famoxadone, metominostrobin and picoxystrobin, cyprodanil, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin and prothioconazole.

Suitable insecticides include thiamethoxam, imidacloprid, acetamiprid, clothianidin, dinotefuran, nitenpyram, fipronil, abamectin, emamectin, bendiocarb, carbaryl, fenoxycarb, isoprocarb, pirimicarb, propoxur, xylylcarb, asulam, chlorpropham, endosulfan, heptachlor, tebufenozide, bensultap, diethofencarb, pirimiphos methyl, aldicarb, methomyl, cyprmethrin, bioallethrin, deltamethrin, lambda cyhalothrin, cyhalothrin, cyfluthrin, fenvalerate, imiprothrin, permethrin and halfenprox.

Suitable plant growth regulators include paclobutrazole and 1-methylcyclopropene.

Suitable safeners include benoxacor, cloquintocet-mexyl, cyometrinil, dichlormid, fenchlorazole-ethyl, fenclorim, flurazole, fluxofenim, mefenpyr-diethyl, MG-191, naphthalic anhydride, and oxabetrinil.

Suitably, the agrochemical is selected from bicyclopyrone, mesotrione, pinoxaden, fomesafen, tralkoxydim, napropamide, amitraz, propanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyclodim, sethoxydim, tepraloxydim, pendimethalin, dinoterb, bifenox, oxyfluorfen, acifluorfen, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron, metoxuron, isopyrazam, mandipropamid, azoxystrobin, trifloxystrobin, kresoxim methyl, famoxadone, metominostrobin and picoxystrobin, cyprodanil, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin, prothioconazole, thiamethoxam, imidacloprid, acetamiprid, clothianidin, dinotefuran, nitenpyram, fipronil, abamectin, emamectin, bendiocarb, carbaryl, fenoxycarb, isoprocarb, pirimicarb, propoxur, xylylcarb, asulam, chlorpropham, endosulfan, heptachlor, tebufenozide, bensultap, diethofencarb, pirimiphos methyl, aldicarb, methomyl, cyprmethrin, bioallethrin, deltamethrin, lambda cyhalothrin, cyhalothrin, cyfluthrin, fenvalerate, imiprothrin, permethrin, halfenprox, paclobutrazole, 1-methylcyclopropene, benoxacor, cloquintocet-mexyl, cyometrinil, dichlormid, fenchlorazole-ethyl, fenclorim, flurazole, fluxofenim, mefenpyr-diethyl, MG-191, naphthalic anhydride and oxabetrinil.

Preferred agrochemical active ingredients are isopyrazam, epoxiconazole, fomesafen, mesotrione, pinoxaden, abamectin, nicosulfuron and azoxystrobin.

The various editions of The Pesticide Manual [especially the 14$^{th}$ and 15$^{th}$ editions] also disclose details of agrochemicals, any one of which may suitably be used in the present invention.

Compositions of the invention may comprise one or more of the agrochemicals described above.

Generally any biologically active ingredient will be present at a concentration of from about 0.000001% to about 90% w/w; preferably from about 0.001% to about 90% w/w.

Agrochemical compositions of the invention may be in the form of a ready-to-use formulation or in concentrate form suitable for further dilution by the end user, and the concentration of agrochemical and compound of formula (I) will be adjusted accordingly. In concentrated form, compositions of the invention typically contain an agrochemical at from 5 to 90% w/w, more preferably from 5 to 75% w/w, even more preferably from 10 to 50% w/w, of the total composition. Ready-to-use compositions of the invention will typically contain an agrochemical at from 0.000001% to 1% w/w, more preferably from 0.000001% to 0.5% w/w, and more preferably still from 0.001% to 0.1% w/w, of the total composition.

In the description of the present invention above, the compounds of formula (I) are described as individual compounds (i.e. n has integral values, relating to a specific number of AO units). Of course, typical alkoxylation reactions will provide a distribution of the number of AO units rather than one single number of units. Therefore, in an alternative aspect of the present invention, there is provided a compound of formula (I), a composition of said compound, methods of making and using said compositions and use of said compounds as herein described except the value of n is defined as an average value [which may be either the mean, the mode or the median value; all three may be very similar to one another] and where such n may be integral or non-integral and is selected from 0 to 45 inclusive; suitably from 0 to 30; preferably from 0 to 20; more preferably from 0 to 10 and even more preferably from 2 to 10.

Typically a specific individual compound of formula (I) will have a concentration of from about 0.0005% to about 90% w/w of the total composition; preferably from about 0.05% to about 90% w/w. When in concentrated form, compositions of the invention typically contain a compound of formula (I) at from 1% to 80% w/w, preferably from 5% to 60% w/w, more preferably from 10% w/w to 40% w/w and even more preferably from 10% w/w to 20% w/w of the total composition. Ready to use compositions of the invention typically contain a compound of formula (I) at from about 0.01% to about 2% w/w of the total composition, more preferably still from about 0.1% to about 1% w/w of the total composition. If the specific individual compound of formula (I) is present with a blend of other compounds of formula (I) due to a variety of values of n, then these concentration ranges for the individual compound may be varied such that the lower limit is reduced by a factor of 10 and the upper limit is reduced by a factor of 2.

Suitably, in a composition of the present invention, typically a compound of formula (I) where n is an average value, will have a concentration of from about 0.0005% to about 90% w/w of the total composition; preferably from about 0.05% to about 90% w/w. When in concentrated form, compositions of the invention typically contain a compound of formula (I) at from 1% to 80% w/w, preferably from 5% to 60% w/w, more preferably from 10% w/w to 40% w/w and even more preferably from 10% w/w to 20% w/w of the total composition. Ready to use compositions of the invention typically contain a compound of formula (I) at from about 0.01% to about 2% w/w of the total composition, more preferably still from about 0.1% to about 1% w/w of the total composition.

Compounds of formula (I) may be formulated in a composition which also contains a biologically active ingredient (for example, an agrochemical) (this is often referred to as a built-in adjuvant formulation) or may be present in a separate composition which does not contain a biologically active ingredient but which is combined with a composition which contains a biologically active ingredient (for example when an end user, such as a farmer, separately adds both a formulation of a biologically active ingredient and a formulation of a compound of formula (I) to a spray-tank of water, in which each formulation either dissolves or disperses prior to being sprayed by the farmer on his crops) (this is often referred to as a tank-mix adjuvant formulation).

Compositions of the invention may be formulated in any suitable manner known to the man skilled in the art. As mentioned above, in one form a composition of the invention is a formulation concentrate which may be diluted or dispersed (typically in water) by an end-user (typically a farmer) in a spray tank prior to application.

Additional formulation components may be formulated with a compound of formula (I) or with a composition according to the present invention. Such additional components include, for example, adjuvants, surfactants, emulsifiers and solvents; standard formulation publications disclose such formulation components suitable for use with the present invention (for example, Chemistry and Technology of Agrochemical Formulations, Ed. Alan Knowles, published by Kluwer Academic Publishers, The Netherlands in 1998; and Adjuvants and Additives: 2006 Edition by Alan Knowles, Agrow Report DS256, published by Informa UK Ltd, December 2006). Further standard formulation components suitable for use with the present invention are disclosed in WO2009/130281A1 (see from page 46, line 5 to page 51, line 40).

Thus, compositions of the present invention may also comprise one or more surfactants or dispersing agents to assist the emulsification of the biologicaly active ingredient on dispersion or dilution in an aqueous medium (dispersant system). The emulsification system is present primarily to assist in maintaining the emulsified biologicaly active ingredient in water. Many individual emulsifiers, surfactants and mixtures thereof suitable for forming an emulsion system for an agrochemical are known to those skilled in the art and a very wide range of choices is available. Typical surfactants that may be used to form an emulsifier system include those containing ethylene oxide, propylene oxide or both ethylene oxide and propylene oxide; aryl or alkylaryl sulphonates and combinations of these with either ethylene oxide or propylene oxide or both; carboxylates and combinations of these with either ethylene oxide or propylene oxide or both. Polymers and copolymers are also commonly used.

Compositions of the present invention may also include solvents, which may have a range of water solubilities. Oils with very low water solubilities may be added to the solvent of the present invention for assorted reasons such as the provision of scent, safening, cost reduction, improvement of emulsification properties and alteration of solubilising power. Solvents with higher water solubility may also be added for various reasons, for instance to alter the ease with which a formulation emulsifies in water, to improve the solubility of a pesticide (agrochemical) or of the other optional additives in the formulation, to change the viscosity of the formulation or to add a commercial benefit.

Other optional ingredients which may be added to the formulation include for example, colourants, scents and other materials which benefit a typical agrochemical formulation.

Compositions of the invention may formulated for example, as emulsion or dispersion concentrates, emulsions in water or oil, as a suspension of particles in an emulsion or oil, as microencapsulated formulations, aerosol sprays or fogging formulations; and these may be further formulated into granular materials or powders, for example for dry application or as water-dispersible formulations. Preferably compositions of the invention will be formulated as, or comprised by an emulsion concentrate (EC), an emulsion in water (EW), a suspension of particles in water (SC), a microcapsule formulation (CS), a soluble liquid (SL), a suspension of particles with an emulsion (SE), a dispersion concentrate (DC) or a suspension of particles in oil (OD).

Compositions of the invention may be used to control pests. The term "pest" as used herein includes insects, fungi, molluscs, nematodes and unwanted plants. Thus, in order to control a pest a composition of the invention may be applied directly to the pest, or to the locus of a pest.

Compositions of the invention also have utility in the seed treatment arena, and thus may be applied as appropriate to seeds.

Various aspects and embodiments of the present invention will now be illustrated in more detail by way of example. It will be appreciated that modification of detail may be made without departing from the scope of the invention.

EXAMPLES

Examples of compounds of formula (I) are given in Table 1 below.

The compounds mentioned below were prepared according to reaction scheme 1 where the alcohol starting materials were commercially available oleyl alcohol ethoxylates known as Brij 92 (oleyl alcohol 2 ethoxylates), Brij 96 (oleyl alcohol 10 ethoxylates) and Brij 98 (oleyl alcohol 20 ethoxylates). The chloroformate starting materials were phenyl chloroformate and benzyl chloroformate which are both commercially available organic reagents. Moreover, the name of each carbonate compound in the table below highlights the nature of both starting materials: B92 stands for Brij 92, B96 stands for Brij 96, B98 stands for Brij 98, -P- stands for phenyl chloroformate and -B- stands for benzyl chloroformate.

TABLE 1

Compounds of formula (I)

| Compound title | Structure |
|---|---|
| B92-P-carbonate | 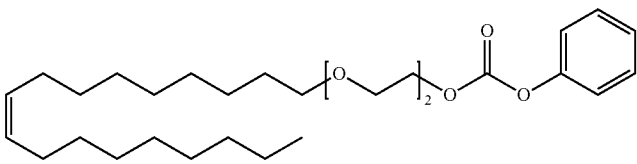 |

TABLE 1-continued

Compounds of formula (I)

| Compound title | Structure |
|---|---|
| B92-B-carbonate | (oleyl chain)–[O–CH₂CH₂]₂–O–C(=O)–O–CH₂–phenyl |
| B96-P-carbonate | (oleyl chain)–[O–CH₂CH₂]₁₀–O–C(=O)–O–phenyl |
| B96-B-carbonate | (oleyl chain)–[O–CH₂CH₂]₁₀–O–C(=O)–O–CH₂–phenyl |
| B98-P-carbonate | (oleyl chain)–[O–CH₂CH₂]₂₀–O–C(=O)–O–phenyl |
| B98-B-carbonate | (oleyl chain)–[O–CH₂CH₂]₂₀–O–C(=O)–O–CH₂–phenyl |

Table 2 summarises the characteristic FTIR bands presented by a terminal-alcohol, which is one of the starting materials, and compounds of formula (I) of Table 1.

TABLE 2

Characteristic FTIR bands for starting materials and selected carbonate compounds

| Compound | Characteristic FTIR bands |
|---|---|
| Starting material: Ethoxylated Oleyl alcohol | O—H: Broad ~3350-3550 cm$^{-1}$ |
| Product: B92-P-carbonate | C=O Sharp ~1764 cm$^{-1}$ |
|  | C—O Sharp ~1261 cm$^{-1}$ |
| Product: B92-B-carbonate | C=O Sharp ~1746 cm$^{-1}$ |
|  | C—O Sharp ~1239 cm$^{-1}$ |
| Product: B96-P-carbonate | C=O Sharp ~1763 cm$^{-1}$ |
|  | C—O Sharp ~1240 cm$^{-1}$ |
| Product: B96-B-carbonate | C=O Sharp ~1739 cm$^{-1}$ |
|  | C—O Sharp ~1242 cm$^{-1}$ |
| Product: B98-P-carbonate | C=O Sharp ~1764 cm$^{-1}$ |
|  | C—O Sharp ~1243 cm$^{-1}$ |
| Product: B98-B-carbonate | C=O Sharp ~1739 cm$^{-1}$ |
|  | C—O Sharp ~1244 cm$^{-1}$ |

Example 1

This example illustrates the use of B92-P-Carbonate, B92-B-Carbonate and B96-P-Carbonate as adjuvants for agrochemical compositions comprising nicosulfuron.

*Setaria viridis*, *Chenopodium album*, *Abutilon theophrasti* and *Digitaria sanguinalis* seeds were sown into standard soil in pots and cultivated under controlled conditions in a glasshouse (at 24/18° C. day/night; 16 hours light; 65% humidity).

When the plants were at the vegetative stage of 3-4 leaves they were sprayed with an aqueous spray solution containing the herbicide nicosulfuron and 0.2% v/v of one of the carbonates, B92-P-Carbonate, B92-B-Carbonate and B96-P-Carbonate (see Table 1).

Each spray solution was applied with a cabinet track-sprayer with a flat fan nozzle (Teejet 11002VS) and an application volume of 200 liter/ha (at 2 bar). Nicosulfuron was applied at either 30 or 60 grams of pesticide per hectare.

The test plants were then grown on, in a glasshouse under controlled conditions (at 24/18° C. day/night; 16 hours light; 65% humidity) and watered twice a day. After 17 and 21 days the test was evaluated for general crop injury (100% equals total damage to a plant; 0% equals no damage to a plant).

The results shown in Table 3 below are mean averages over the two rates of nicosulfuron, three replicates and the two assessment timings, and are compared to the efficacy of nicosulfuron in the absence of an adjuvant and nicosulfuron in the presence of the commercially available tank-mix adjuvant, Atplus411F® (at 0.2% by volume).

TABLE 3

Mean percentage kill results for nicolsulfuron in the presence and absence of 0.2% by volume B92-P-Carbonate, B92-B-Carbonate, B96-P-Carbonate and Atplus 411F ®.
A standard Tukey HSD test was carried out to assess whether each result was statistically different from the other results and this is expressed as a letter: tests with the same letter are not statistically different ($p < 0.05$).

| Treatment | SETVI | DIGSA | CHEAL | ABUTH | Mean across species |
|---|---|---|---|---|---|
| Nicosulfuron + B92-P-Carbonate | 90.8 | 84.2 | 77.5 | 50.0 | 75.6 A |
| Nicosulfuron + B92-B-Carbonate | 86.7 | 86.7 | 79.2 | 54.2 | 76.7 A |
| Nicosulfuron + B96-P-Carbonate | 96.2 | 78.3 | 80.0 | 43.3 | 74.5 A |
| Nicosulfuron + Atplus411F | 84.2 | 83.3 | 73.3 | 56.7 | 74.4 A |
| Nicosulfuron | 79.2 | 31.7 | 36.7 | 48.3 | 49.0 B |

Example 2

This example illustrates the use of B92-P-Carbonate, B92-B-Carbonate and B96-P-Carbonate as adjuvants for agrochemical compositions comprising fomesafen.

*Setaria viridis*, *Chenopodium album*, *Abutilon theophrasti* and *Ipomea hederacea* seeds were sown into standard soil in pots and cultivated under controlled conditions in a glasshouse (at 24/18° C. day/night; 16 hours light; 65% humidity).

When the plants were at the vegetative stage of 2-4 leaves they were sprayed with an aqueous spray solution containing the herbicide fomesafen and 0.2% v/v of one of the carbonates B92-P-Carbonate, B92-B-Carbonate and B96-P-Carbonate (see Table 1).

The spray solution was applied with a cabinet track-sprayer with a flat fan nozzle (Teejet 11002VS) and an application volume of 200 liter/ha (at 2 bar). Fomesafen was applied at either 60 or 120 grams of pesticide per hectare.

The test plants were then grown on, in a glasshouse under controlled conditions (at 24/18° C. day/night; 16 hours light; 65% humidity) and watered twice a day. After 14 and 21 days the test was evaluated for general crop injury (100% equals total damage to a plant; 0% equals no damage to a plant).

The results shown in Table 4 below are mean averages over the two rates of fomesafen, three replicates and the two assessment timings, and are compared to the efficacy of fomesafen in the absence of an adjuvant, and fomesafen in the presence of the commercially available tank-mix adjuvant, Turbocharge®, which was used at an application rate of 0.5% by volume of the spray tank.

TABLE 4

Mean percentage kill results for fomesafen in the presence and absence of 0.2% v/v of B92-P-Carbonate, B92-B-Carbonate, B96-P-Carbonate and 0.5% v/v Turbocharge ®.
A standard Tukey HSD test was carried out to assess whether each result was statistically different from the other results and this is expressed as a letter: tests with the same letter are not statistically different ($p < 0.05$).

| Treatment | SETVI | CHEAL | ABUTH | COMBEN | Mean across species |
|---|---|---|---|---|---|
| Fomesafen + B92-P-Carbonate | 26.7 | 83.3 | 62.5 | 30.0 | 50.6 AB |
| Fomesafen + B92-B-Carbonate | 41.7 | 85.8 | 41.7 | 20.0 | 47.3 B |
| Fomesafen + B96-P-Carbonate | 25.0 | 86.7 | 48.3 | 28.3 | 47.1 B |
| Fomesafen + Turbocharge | 60.0 | 85.8 | 59.2 | 38.3 | 47.1 A |
| Fomesafen | 19.2 | 58.3 | 23.3 | 15.0 | 29.0 C |

Example 3

This example illustrates the use of se of B92-P-Carbonate, B92-B-Carbonate and B96-P-Carbonate as adjuvants for agrochemical compositions comprising mesotrione.

*Brachiaria plantaginea*, *Digitaria sanguinalis*, *Commelina benghalensis* and *Polygonum convulvulus* seeds were sown into standard soil in pots and cultivated under controlled conditions in a glasshouse (at 24/18° C. day/night; 16 hours light; 65% humidity).

When the plants were at the vegetative stage of 2-4 leaves they were sprayed with an aqueous spray solution containing the herbicide mesotrione and 0.2% v/v of one of the carbonates B92-P-Carbonate, B92-B-Carbonate and B96-P-Carbonate (see Table 1).

The spray solution was applied with a cabinet track-sprayer with a flat fan nozzle (Teejet 11002VS) and an application volume of 200 liter/ha (at 2 bar). Mesotrione was applied at either 30 or 60 grams of pesticide per hectare.

The test plants were then grown on, in a glasshouse under controlled conditions (at 24/18° C. day/night; 16 hours light; 65% humidity) and watered twice a day. After 14 and 21 days the test was evaluated for general crop injury (100% equals total damage to a plant; 0% equals no damage to a plant).

The results shown in Table 5 below are mean averages over the two rates of mesotrione, three replicates and the two assessment timings, and are compared to the efficacy of mesotrione in the absence of an adjuvant, and mesotrione in the presence of the commercially available tank-mix adjuvant, Tween 20 ®+Rhodasurf DA/630-E® (2:1 in water).

TABLE 5

Mean percentage kill results for mesotrione in the presence and absence of 0.2% of B92-P-Carbonate, B92-B-Carbonate, B96-P-Carbonate or 0.5% Tween 20 ® + Rhodasurf DA/630-E ®. A standard Tukey HSD test was carried out to assess whether each result was statistically different from the other results and this is expressed as a letter: tests with the same letter are not statistically different ($p < 0.05$).

| Treatment | BRAPL | DIGSA | COMBEN | POLCONV | Mean across species |
|---|---|---|---|---|---|
| Mesotrione + B92-P-Carbonate | 63.3 | 74.2 | 64.2 | 77.5 | 69.8 A |
| Mesotrione + B92-B-Carbonate | 52.5 | 67.5 | 63.3 | 71.7 | 63.8 A |

TABLE 5-continued

Mean percentage kill results for mesotrione in the presence and absence of 0.2% of B92-P-Carbonate, B92-B-Carbonate, B96-P-Carbonate or 0.5% Tween 20 ® + Rhodasurf DA/630-E ®. A standard Tukey HSD test was carried out to assess whether each result was statistically different from the other results and this is expressed as a letter: tests with the same letter are not statistically different (p < 0.05).

| Treatment | BRAPL | DIGSA | COMBEN | POLCONV | Mean across species |
|---|---|---|---|---|---|
| Mesotrione + B96-P-Carbonate | 40.8 | 75.0 | 61.7 | 71.7 | 62.3 A |
| Mesotrione Tween 20 ® + Rhodasurf DA/630-E ® | 45.8 | 75.8 | 69.2 | 76.7 | 66.9 A |
| Mesotrione | 1.7 | 44.2 | 53.3 | 70.8 | 42.5 B |

Example 4

This example illustrates the use of B92-P-Carbonate, B92-B-Carbonate and B96-P-Carbonate as adjuvants for agrochemical compositions comprising pinoxaden.

*Avena fatua, Lolium perenne, Setaria viridis* and *Alopecurus myosuroides* seeds were sown into standard soil in pots and cultivated under controlled conditions in a glasshouse (at 20/16° C. day/night; 15 hours light; 65% humidity).

When the plants were at the vegetative stage of 2-3 leaves they were sprayed with an aqueous spray solution containing the herbicide pinoxaden and 0.2% v/v of one of the carbonates B92-P-Carbonate, B92-B-Carbonate and B96-P-Carbonate (see Table 1).

The spray solution was applied with a cabinet tracksprayer with a flat fan nozzle (Teejet 11002VS) and an application volume of 200 liter/ha (at 2 bar). Pinoxaden was applied at either 7.5 or 15 grams of pesticide per hectare. The test plants were then grown on in a glasshouse under controlled conditions (at 24/18° C. day/night; 16 hours light; 65% humidity) and watered twice a day. After 14 and 21 days the test was evaluated for general crop injury (100% equals total damage to a plant; 0% equals no damage to a plant).

The results shown in Table 6 below are mean averages over the two rates of pinoxaden, three replicates and the two assessment timings, and are compared to the efficacy of pinoxaden in the absence of an adjuvant, and pinoxaden in the presence of the tris(2-ethylhexyl)phosphate [TEHP, used as a standard, for comparative purposes] (at 0.2% by volume).

TABLE 6

Mean percentage kill results for pinoxaden in the presence and absence of 0.2% B92-P-Carbonate, B92-B-Carbonate, B96-P-Carbonate and tris(2-ethylhexyl)phosphate. A standard Tukey HSD test was carried out to assess whether each result was statistically different from the other results and this is expressed as a letter: tests with the same letter are not statistically different (p < 0.05).

| Treatment | AVENA FATUA | LOLIUM PERENNE | SETARIA VIRIDIS | ALOPECURUS MYOSUROIDES | Mean across species |
|---|---|---|---|---|---|
| Pinoxaden + B92-P-Carbonate | 93.7 | 57.5 | 96.2 | 60.8 | 77.0 AB |
| Pinoxaden + B92-B-Carbonate | 90.0 | 55.8 | 98.2 | 54.2 | 74.5 AB |
| Pinoxaden + B96-P-Carbonate | 90.8 | 46.7 | 92.8 | 43.3 | 68.4 B |
| Pinoxaden + TEHP | 91.2 | 82.5 | 98.7 | 65.0 | 84.3 A |
| Pinoxaden | 10.0 | 1.7 | 0 | 0 | 2.9 C |

Further examples of compounds of formula (I) are given in Table 7 below.

TABLE 7

Compounds of formula (I)

| Compound code | Structure | Compound description |
|---|---|---|
| A | (structure shown) | Glycerol-$(CO_3$-ethyl$)_3$ |

TABLE 7-continued

Compounds of formula (I)

| Compound code | Structure | Compound description |
|---|---|---|
| B | (structure) | Glycerol-$(CO_3$-2-ethylhexyl$)_3$ |
| C | (structure) n = 6 | Glycerol-(6EO-$CO_3$-2-ethylhexyl$)_3$ |
| D | (structure) n = 6 | Glycerol-(6EO-$CO_3$-phenyl$)_3$ |
| E | (structure) n = 10 | Oleyl 10EO-($CO_3$-2-ethylhexyl) |

Example 5

The carbonate compounds A, B, C, D and E were tested as adjuvants for agrochemical compositions comprising nicosulfuron.

*Setaria viridis*, *Chenopodium album*, *Abutilon theophrasti* and *Digitaria sanguinalis* seeds were sown into standard soil in pots and cultivated under controlled conditions in a glasshouse (at 24/18° C. day/night; 16 hours light; 65% humidity).

When the plants were at the vegetative stage of 3-4 leaves they were sprayed with an aqueous spray solution containing the herbicide nicosulfuron and 0.2% v/v of one of the carbonates A, B, C, D and E (see Table 7).

Each spray solution was applied with a cabinet track-sprayer with a flat fan nozzle (Teejet 11002VS) and an application volume of 200 liter/ha (at 2 bar). Nicosulfuron was applied at either 15 or 60 grams of pesticide per hectare.

The test plants were then grown on, in a glasshouse under controlled conditions (at 24/18° C. day/night; 16 hours light; 65% humidity) and watered twice a day. After 22 days the test was evaluated for general crop injury or phytotoxicity (100% equals total damage to a plant; 0% equals no damage to a plant).

The results shown in Table 8 below are mean averages over the two rates of nicosulfuron, the three replicates and the four plant species, and are compared to the efficacy of nicosulfuron in the absence of an adjuvant and nicosulfuron in the presence of the commercially available tank-mix adjuvant, Atplus411F® (at 0.5% by volume).

The results in Table 8 show that the carbonate compounds A, B, C and D increase the efficacy of nicosulfuron compositions and that the carbonate compounds C and D are particularly effective as adjuvants for nicosulfuron. The results in Table 9 show that compound E is a particularly effective adjuvant for nicosulfuron.

TABLE 8

Mean percentage kill results for nicosulfuron in the presence and absence of 0.2% by volume of compounds A, B, C, and D and 0.5% by volume Atplus 411F ®.

| Treatment | Mean % phytotoxicity |
| --- | --- |
| Nicosulfuron + No Adjuvant | 36.46 |
| Nicosulfuron + Atplus 411F ® | 67.92 |
| Nicosulfuron + compound D | 61.67 |
| Nicosulfuron + compound C | 61.26 |
| Nicosulfuron + compound A | 48.55 |
| Nicosulfuron + compound B | 55.63 |

TABLE 9

Mean percentage kill results for nicosulfuron in the presence and absence of 0.2% by volume of compound E and 0.5% by volume Atplus 411F ®.

| Treatment | Mean % Phytotoxicity |
| --- | --- |
| Nicosulfuron + No Adjuvant | 28.3 |
| Nicosulfuron + Atplus 411F | 73.0 |
| Nicosulfuron + compound E | 68.8 |

Example 6

The carbonate compounds A, B, C, and D were tested as adjuvants for agrochemical compositions comprising mesotrione.

*Brachiaria plantaginea*, *Digitaria sanguinalis*, *Commelina benghalensis* and *Polygonum convulvulus* seeds were sown into standard soil in pots and cultivated under controlled conditions in a glasshouse (at 24/18° C. day/night; 16 hours light; 65% humidity).

When the plants were at the vegetative stage of 2-4 leaves they were sprayed with an aqueous spray solution containing the herbicide mesotrione and 0.2% v/v of one of the carbonates A, B, C and D (see Table 7).

The spray solution was applied with a cabinet track-sprayer with a flat fan nozzle (Teejet 11002VS) and an application volume of 200 liter/ha (at 2 bar). Mesotrione was applied at either 30 or 60 grams of pesticide per hectare.

The test plants were then grown on, in a glasshouse under controlled conditions (at 24/18° C. day/night; 16 hours light; 65% humidity) and watered twice a day. After 25 days the test was evaluated for general crop injury or phytotoxicity (100% equals total damage to a plant; 0% equals no damage to a plant).

The results shown in Table 10 below are mean averages over the two rates of mesotrione, the three replicates and the four plant species and are compared to the efficacy of mesotrione in the absence of an adjuvant, and mesotrione in the presence of the commercially available tank-mix adjuvant, Tween 20 ®+Rhodasurf DA/630-E® (combined in a 2:1 ratio) at 0.5% by volume.

The results in Table 10 show that the carbonate compounds A and B are particularly effective at increasing the efficacy of mesotrione compositions.

TABLE 10

Mean percentage kill results for mesotrione in the presence and absence of 0.2% of compounds A, B, C and D or 0.5% Tween ® + Rhodasurf ®

| Treatment | Mean % Phytotoxicity |
| --- | --- |
| Mesotrione + No Adjuvant | 33.71 |
| Mesotrione + Tween 20 ® + Rhodasurf DA/630-E ® (in 2:1 ratio) | 69.17 |
| Mesotrione + compound D | 37.71 |
| Mesotrione + compound C | 45.50 |
| Mesotrione + compound A | 54.17 |
| Mesotrione + compound B | 60.52 |

Example 7

The carbonate compounds A, B, C, D and E were tested as adjuvants for agrochemical compositions comprising pinoxaden.

*Avena fatua*, *Lolium perenne*, *Setaria viridis* and *Alopecurus myosuroides* seeds were sown into standard soil in pots and cultivated under controlled conditions in a glasshouse (at 20/16° C. day/night; 15 hours light; 65% humidity).

When the plants were at the vegetative stage of 2-3 leaves they were sprayed with an aqueous spray solution containing the herbicide pinoxaden and 0.2% v/v of one of the carbonates A, B, C, D and E (see Table 7).

The spray solution was applied with a cabinet track-sprayer with a flat fan nozzle (Teejet 11002VS) and an application volume of 200 liter/ha (at 2 bar). Pinoxaden was applied at either 7.5 or 15 grams of pesticide per hectare.

The test plants were then grown on. in a glasshouse under controlled conditions (at 24/18° C. day/night; 16 hours light; 65% humidity) and watered twice a day. After 22 days the test was evaluated for general crop injury or phytotoxicity (100% equals total damage to a plant; 0% equals no damage to a plant).

The results shown in Table 11 below are mean averages over the two rates of pinoxaden, the three replicates and the four plant species, and are compared to the efficacy of pinoxaden in the absence of an adjuvant, and pinoxaden in the presence of tris(2-ethylhexyl)phosphate, used as a standard adjuvant for comparative purposes (at 0.2% by volume).

The results in Table 11 show that the carbonate compound B is the most effective at increasing the efficacy of the pinoxaden composition. The results in Table 12 show that compound E is effective as an adjuvant for pinoxaden.

TABLE 11

Mean percentage kill results for pinoxaden in the presence and absence of 0.2% by volume of compounds A, B, C and D and 0.2% by volume tris(2-ethylhexyl)phosphate.

| Treatment | Mean % Phytotoxicity |
| --- | --- |
| Pinoxaden + No Adjuvant | 4.25 |
| Pinoxaden + tris(2-ethylhexyl)phosphate. | 85.80 |
| Pinoxaden + compound D | 6.96 |
| Pinoxaden + compound C | 36.13 |
| Pinoxaden + compound A | 14.97 |
| Pinoxaden + compound B | 58.80 |

TABLE 12

Mean percentage kill results for pinoxaden in the presence and absence of 0.2% by volume of compound E and 0.2% by volume tris(2-ethylhexyl)phosphate.

| Treatment | Mean % Phytotoxicity |
| --- | --- |
| Pinoxaden + No Adjuvant | 0 |
| Pinoxaden + tris(2-ethylhexyl)phosphate. | 89.3 |
| Pinoxaden + compound E | 65.4 |

Example 8

The carbonate compound E was tested as an adjuvant for agrochemical compositions comprising isopyrazam.

Wheat plants were inoculated with the fungus *Septoria tritici*. Four days after inoculation the plants were sprayed with a diluted suspension concentrate formulation of the fungicide isopyrazam at rates of 3, 10, 30 and 100 mg of the fungicide per liter of spray solution, using a laboratory track sprayer which delivered the spray at a rate of 200 liters per hectare. Spray tests were also carried out with a diluted suspension concentrate additionally comprising the carbonate compound E (see Table 7) added to the spray solution at a rate of 0.1% v/v, based on the quantity of spray liquor. The leaves of the plants were assessed visually 12 days after the spray application and the damage was expressed as the percentage of the leaf area infected. Each spray test was replicated four times across the four application rates.

The results shown in Table 13 below are mean averages over the four rates of isopyrazam and the four replicates, and are compared to the efficacy of isopyrazam in the absence of an adjuvant, and isopyrazam in the presence of oleyl ethoxylate 20EO butyl end capped adjuvant used as a standard adjuvant for comparative purposes (at 0.1% by volume).

As can be seen from Table 13 the inclusion of the carbonate compound E with isopyrazam resulted in a significant reduction in the percentage of infection by *S. tritici* in comparison to that achieved by the isopyrazam in the absence of an adjuvant. The carbonate E is as effective as an adjuvant for the isopyrazam composition as the standard adjuvant oleyl ethoxylate 20EO butyl end capped.

TABLE 13

Mean % infection of wheat plants with *S. tritici* treated with isopyrazam in the presence and absence of 0.1% by volume of compound E and 0.1% by volume oleyl ethoxylate 20EO butyl end capped

| Treatment | Mean % infection |
| --- | --- |
| Isopyrazam | 65.1 |
| Isopyrazam plus Oleyl 20EO butyl end capped | 44.3 |
| Isopyrazam plus compound E | 43.5 |

Example 9

The carbonate compound E was tested as an adjuvant for agrochemical compositions comprising epoxiconazole.

Wheat plants were inoculated with the fungus *Septoria tritici*. Four days after inoculation the plants were sprayed with a diluted suspension concentrate formulation of the fungicide epoxiconazole at rates of 3, 10, 30 and 100 mg of the fungicide per liter of spray solution, using a laboratory track sprayer which delivered the spray at a rate of 200 liters per hectare. Spray tests were also carried out with a diluted suspension concentrate additionally comprising the carbonate compound E (see Table 7) added to the spray solution at a rate of 0.1% v/v, based on the quantity of spray liquor. The leaves of the plants were assessed visually 12 days after the spray application and the damage was expressed as the percentage of the leaf area infected. Each spray test was replicated four times across the four application rates.

The results shown in Table 14 below are mean averages over the four rates of epoxiconazole and the four replicates, and are compared to the efficacy of epoxiconazole in the absence of an adjuvant, and epoxiconazole in the presence of oleyl ethoxylate 20EO butyl end capped adjuvant used as a standard adjuvant for comparative purposes (at 0.1% by volume).

As can be seen from Table 14 the inclusion of the carbonate compound E wites epoxiconazole resulted in a significant reduction in the percentage of infection by *S. tritici* in comparison to that achieved by the epoxiconazole in the absence of an adjuvant.

TABLE 14

Mean % infection of wheat plants with *S. tritici* treated with epoxiconazole in the presence and absence of 0.1% by volume of compound E and 0.1% by volume oleyl ethoxylate 20EO butyl end capped

| Treatment | Mean % infection |
| --- | --- |
| Epoxiconazole | 40.0 |
| Epoxiconazole plus Oleyl 20EO butyl end capped | 10.3 |
| Epoxiconazole plus compound E | 15.6 |

Example 10

The carbonate compounds B92-P-carbonate and B96-P-carbonate were tested as adjuvants for agrochemical compositions comprising isopyrazam.

Wheat plants were inoculated with the fungus *Septoria tritici*. Four days after inoculation the plants were sprayed with a diluted suspension concentrate formulation of the fungicide isopyrazam at rates of 3, 10, 30 and 100 mg of the fungicide per liter of spray solution, using a laboratory track sprayer which delivered the spray at a rate of 200 liters per hectare. Spray tests were also carried out with diluted suspension concentrates additionally comprising the carbonates B92-P-carbonate and B96-P-carbonate (see Table 1) which were added to the spray solution at a rate of 0.1% v/v, based on the quantity of spray liquor. The leaves of the plants were assessed visually 14 days after the spray application and the damage was expressed as the percentage of the leaf area infected. Each spray test was replicated twelve times across the four application rates.

The results shown in Table 15 below are mean averages over the four rates of isopyrazam and the twelve replicates, and are compared to the efficacy of isopyrazam in the absence of an adjuvant, and isopyrazam in the presence of oleyl ethoxylate 20EO butyl end capped which was used as a standard for comparative purposes (at 0.1% by volume).

As can be seen from Table 15 the inclusion of either of the carbonate compounds with isopyrazam resulted in a significant reduction in the percentage of infection by *S. tritici* in comparison to that achieved by the isopyrazam in the absence of an adjuvant. The two carbonate adjuvants also displayed similar effectiveness as the standard adjuvant.

TABLE 15

Mean % infection of wheat plants with *S. tritici* treated with isopyrazam in the presence and absence of 0.1% by volume of B92-P-carbonate, B96-P-carbonate and 0.1% by volume oleyl ethoxylate 20EO butyl end capped.

| Treatment | Mean % infection |
| --- | --- |
| Isopyrazam | 76.9 |
| Isopyrazam plus oleyl 20EO butyl end capped | 29.6 |
| Isopyrazam plus Brij 92-P-carbonate | 41.8 |
| Isopyrazam plus Brij 96-P-carbonate | 28 |

Example 11

The carbonate compounds B92-P-carbonate and B96-P-carbonate were tested as adjuvants for agrochemical compositions comprising epoxiconazole.

Wheat plants were inoculated with the fungus *Septoria tritici*. Four days after inoculation the plants were sprayed with a diluted suspension concentrate formulation of the fungicide epoxiconazole at rates of 3, 10, 30 and 100 mg of the fungicide per liter of spray solution, using a laboratory track sprayer which delivered the spray at a rate of 200 liters per hectare. Spray tests were also carried out with a diluted suspension concentrate additionally comprising the carbonates B92-P-carbonate and B96-P-carbonate (see Table 1) added to the spray solution at a rate of 0.1% v/v, based on the quantity of spray liquor. The leaves of the plants were assessed visually 14 days after the spray application and the damage was expressed as the percentage of the leaf area infected. Each spray test was replicated twelve times across the four application rates.

The results shown in Table 16 below are mean averages over the four rates of epoxiconazole and the twelve replicates, and are compared to the efficacy of epoxiconazole in the commercial product Opus® 125, and epoxiconazole in the presence of oleyl ethoxylate 20EO butyl end capped which was used as a standard for comparative purposes (at 0.1% by volume).

As can be seen from Table 16 the inclusion of either carbonate compound with epoxiconazole resulted in a significant reduction in the percentage of infection by *S. tritici* in comparison to that achieved by the commercial formulation of epoxiconazole.

TABLE 16

Mean % infection of wheat plants with *S. tritici* treated with epoxiconazole in the presence and absence of 0.1% by volume of the compounds B92-P-carbonate and B96-P-carbonate and 0.1% by volume of oleyl ethoxylate 20EO butyl end capped.

| Treatment | Mean % infection |
| --- | --- |
| Opus ® 125 | 40.3 |
| Epoxiconazole plus oleyl 20EO butyl end capped | 9.1 |
| Epoxiconazole plus Brij-92-P-carbonate | 28.7 |
| Epoxiconazole plus Brij-96-P-carbonate | 24.4 |

The invention claimed is:

1. A composition comprising an agrochemical and a compound of formula (I)

$$\left[ Q-O-\underset{\underset{O}{\|}}{C}-O-(AO)_n-R \right]_m \quad (I)$$

wherein each A is independently selected from $C_{1-10}$ alkanediyl;

n is an integer selected from 0 to 45 inclusive; and m is an integer selected from 1, 2, 3 and 4;

R is a branched or linear $C_1$-$C_{24}$ hydrocarbon either fully saturated or comprising up to three double bonds or is a $C_3$-$C_8$ fully saturated cyclic group; and R is substituted 1, 2, 3 or 4 times as defined by the value of m; and Q is a branched or linear $C_1$-$C_{24}$ hydrocarbon either fully saturated or comprising up to three double bonds or is phenyl or is benzyl or is a $C_3$-$C_8$ fully saturated cyclic group; provided that when m is 1 and n is zero, Q and R are not both selected from a branched or linear $C_1$-$C_{24}$ hydrocarbon either fully saturated or comprising up to three double bonds.

2. A composition as claimed in claim 1 wherein m is 1, 2 or 3.

3. A composition as claimed in claim 1 wherein each A is independently selected from $C_2$-$C_4$ alkanediyl.

4. A composition as claimed in claim 1 wherein n is an integer selected from 0 to 30 inclusive.

5. A composition as claimed in claim 1 where Q is a branched or linear $C_1$-$C_{24}$ hydrocarbon either fully saturated or comprising up to three double bonds or is phenyl or is benzyl.

6. An composition as claimed in claim 1 wherein the agrochemical is present at a concentration in the range from about 0.000001% to about 90% w/w.

7. A composition as claimed in claim 1 where the concentration of the compound of formula (I) is from about 0.0005% w/w to about 90% w/w of the total composition.

8. A composition as claimed in claim 1 where the composition is an emulsion concentrate (EC), an emulsion in water (EW), a suspension of particles in water (SC), a soluble liquid (SL), a microcapsule formulation (CS), a suspension of particles with an emulsion (SE), a dispersion concentrate (DC), a suspension of particles in oil (OD), a water dispersible granule (WG), a soluble granule (SG) or a wettable powder (WP).

9. A method of controlling a pest, comprising applying a composition as claimed in claim 1 to said pest or a locus of said pest.

10. A method of making a composition as claimed in claim 1 comprising providing:
 (i) an agrochemical; and
 (ii) a compound of formula (I) as defined in claim 1;
 and combining ingredients (i) and (ii).

* * * * *